(12) United States Patent
Bhandari et al.

(10) Patent No.: US 11,141,094 B2
(45) Date of Patent: Oct. 12, 2021

(54) METHOD AND SYSTEM FOR ASSESSING A BALANCE AND POSTURE OF A SUBJECT

(71) Applicants: Rajneesh Bhandari, Jaipur (IN); Anita Bhandari, Jaipur (IN)

(72) Inventors: Rajneesh Bhandari, Jaipur (IN); Anita Bhandari, Jaipur (IN)

(73) Assignee: Neuroequilibrium Diagnostic Systems Private Limited

( * ) Notice: Subject to any disclaimer, the term of this patent is extended or adjusted under 35 U.S.C. 154(b) by 102 days.

(21) Appl. No.: 16/442,434

(22) Filed: Jun. 14, 2019

(65) Prior Publication Data

US 2020/0229751 A1  Jul. 23, 2020

(30) Foreign Application Priority Data

Jan. 17, 2019 (IN) .............................. 201911002133

(51) Int. Cl.
*A61B 5/00* (2006.01)
*A61B 5/11* (2006.01)
*G16H 50/20* (2018.01)
*A61B 3/113* (2006.01)

(52) U.S. Cl.
CPC .......... *A61B 5/4023* (2013.01); *A61B 5/1116* (2013.01); *A61B 5/6803* (2013.01); *A61B 3/113* (2013.01); *A61B 5/6814* (2013.01); *G16H 50/20* (2018.01)

(58) Field of Classification Search
CPC ............ A63F 2300/8082; G16H 50/20; A61B 5/4023; A61B 5/1116; A61B 5/6803; A61B 2562/0219; A61B 2562/0261; A61B 3/113
See application file for complete search history.

(56) References Cited

U.S. PATENT DOCUMENTS 9,526,443 B1 * 12/2016 Berme .................... G06F 3/147
2017/0213145 A1 * 7/2017 Pathak .................. G06N 7/005

FOREIGN PATENT DOCUMENTS

CN 206228330 U * 6/2017

* cited by examiner

*Primary Examiner* — Carl H Layno
*Assistant Examiner* — Aya Ziad Bakkar
(74) *Attorney, Agent, or Firm* — Farrell Patent Law PC; Mark Farrell

(57) ABSTRACT

A method and system for assessing balance and posture of a subject by employing virtual reality (VR) or augmented reality (AR) headgear is provided. The system includes memory, a processor, and the VR/AR headgear, providing an immersive environment. The VR/AR headgear includes a display for providing a plurality of visual stimuli. A gyroscope and an inertial measurement unit detect head movements and body sway of the subject in response to the plurality of visual stimuli. An eye tracking unit tracks eye movement of the subject in response to the plurality of visual stimuli. A base plate with sensors can measure center of gravity of the subject in response to movements of the base plate. A machine learning model then deciphers patterns based on measurement data from the gyroscope, inertial measurement unit, eye tracking unit, and base plate. A comprehensive report pertaining to the subject's posture and balance is then generated.

14 Claims, 5 Drawing Sheets

METHOD AND SYSTEM FOR ASSESSING A BALANCE AND POSTURE OF A SUBJECT

FIELD OF THE INVENTION

The invention generally relates to a method and system for assessing a balance and posture of a subject. More specifically, the invention relates to a method and system for assessing balance and posture of the subject using a virtual reality or an augmented reality headgear, and further utilizing a machine learning model to assess and generate a comprehensive report pertaining to the assessment of posture and stability of the subject.

BACKGROUND OF THE INVENTION

Computerized Dynamic Posturography (CDP) is a non-invasive specialized clinical assessment technique used to quantify the central nervous system adaptive mechanisms (sensory, motor and central) involved in the control of posture and balance, both in normal conditions such as in physical education and sports training, and abnormal conditions particularly in the diagnosis of balance disorders and in physical therapy and postural re-education.

Due to the complex interactions among sensory, motor, and central processes involved in posture and balance, CDP requires different protocols to differentiate among the many defects and impairments which may affect a subject's or a patient's posture control system. Therefore, CDP addresses these challenges using several combinations of visual and support surface stimuli and parameters.

Clinical applications for CDP were first described by L. M. Nashner in 1982, and the first commercially available testing system was developed in 1986, when NeuroCom International, Inc., launched the EquiTest system.

Traditional methods of CDP include static posturography and dynamic posturography.

Static posturography is carried out by placing the patient in a standing posture on a fixed instrumented platform such as a force plate connected to sensitive detectors such as force and movement transducers, which detect the tiny oscillations of the body of patient.

Dynamic posturography, on the other hand, differentiates from static posturography generally by using a special apparatus with a movable horizontal platform. As the patient makes small movements, the measurements related to the movements are transmitted in real-time to a computer. The computer is also used to command electric motors which move the force plate in the horizontal direction (translational motion) as well as to incline it (rotations). The base has electric motors for forward and backward movement.

Thus, the posturography test protocols generate a sequence of standardized motions in the support platform to desequilibrate the patient's posture in an orderly and reproducible way. The platform is contained within an enclosure which is used to generate apparent visual surround motions. These stimuli are calibrated relative to the patient's height and weight. A computer software produces detailed graphics and reports which are then be compared with normal ranges.

Existing techniques for static and dynamic posturography use a flat screen or a curved screen to display apparent visual surround motions. Further, these techniques use force plates for measuring shift in center of gravity.

There are several limitations or drawbacks of these techniques including the use of curved screens to generate images which are expensive and these techniques are not fully immersive as the patient can see beyond the screen. Further, implementation of these techniques requires a lot of space, and force plates are expensive for use.

Also, these techniques do not possess any means for measuring head movement of a subject, which is a vital parameter to determine sway and stability of the patient. Furthermore, in these techniques, the patient is subjected to specific motions such as a translation motion during the testing. Such motions are not experienced in normal life while parameters are required to be measured during normal gait.

Therefore, in light of the above, there exists a need for a method and system of CDP for effectively assessing the balance and posture of a patient or subject.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1:
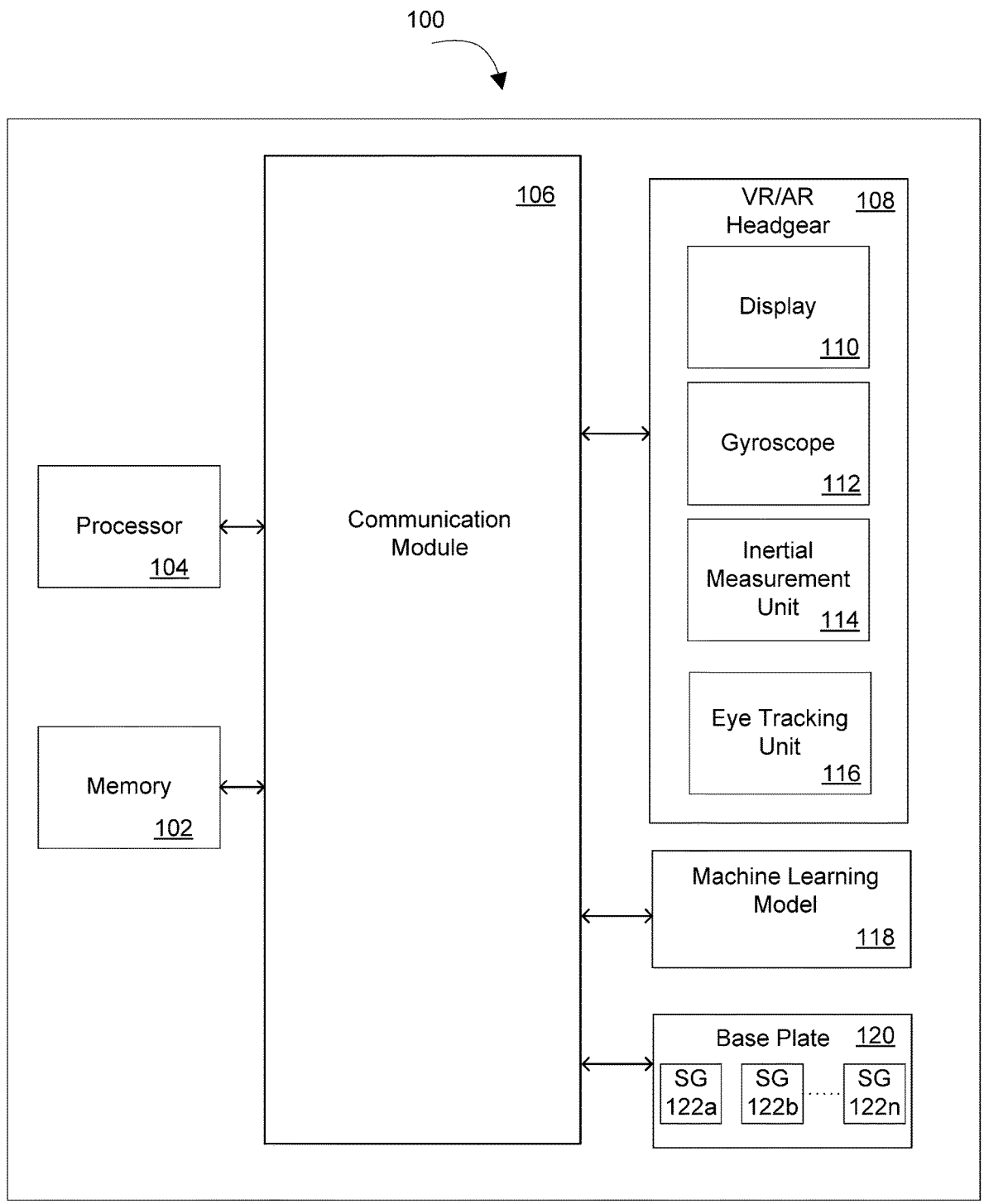
FIG. 1 illustrates a system for assessing a balance and posture of a subject in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of method steps and system components related to assessing balance and posture of a subject using a virtual reality or an augmented reality headgear, and further utilizing a machine learning model to assess and generate a comprehensive report pertaining to the assessment of posture and stability of the subject.

Accordingly, the system components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article or composition that comprises a list of elements does not include only those elements but may include other elements not expressly listed or inherent to such process, method, article or composition. An element proceeded by "comprises . . . a" does not, without more constraints, preclude the existence of additional identical elements in the process, method, article or composition that comprises the element.

Various embodiments of the invention provide a method and system for assessing a balance and posture of a subject by employing a virtual reality (VR) or an augmented reality (AR) headgear. The system includes a memory, a processor communicatively coupled to the memory and a VR/AR headgear communicatively coupled to the memory and the processor for providing an immersive environment to the subject. The VR/AR headgear includes a display for providing a plurality of visual stimuli to the subject. The VR/AR headgear further includes a gyroscope and an inertial measurement unit for detecting head movements and body sway of the subject in response to the plurality of visual stimuli provided to the subject on the display. The VR/AR headgear also includes an eye tracking unit for tracking eye movements of the subject in response to the plurality of visual stimuli provided to the subject on the display. A machine learning model is then used to decipher normal patterns and abnormal patterns based on measurement data from the gyroscope, measurement data from the inertial measurement unit, and measurement data from the eye tracking unit. A comprehensive report pertaining to the subject's posture and balance is then generated based on measurement data from the gyroscope, measurement data from the inertial measurement unit, and measurement data from the eye tracking unit, using the machine learning model.

FIG. 1 illustrates a system 100 for assessing a balance and posture of a subject in accordance with an embodiment of the invention.

As illustrated in FIG. 1, system 100 includes a memory 102 and a processor 104 communicatively coupled to memory 102. Memory 102 and processor 104 further communicate with one or more components via a communication module 106. Communication module 106 may be configured to transmit data between modules, engines, databases, memories, and other components of system 100 for use in performing the functions discussed herein. Communication module 106 may include one or more communication types and utilize various communication methods for communication within system 100.

System 100 includes a VR/AR headgear 108 to be worn by a subject undergoing balance and posture assessment, and provides an immersive environment to the subject.

VR/AR headgear 108 further includes a display 110 communicatively coupled to memory 102 and processor 104. Display 110 is configured to display a plurality of visual stimuli to the subject.

VR/AR headgear 108 further includes a gyroscope 112 and an inertial measurement unit 114 for detecting head movement and body sway of the subject in response to the plurality of visual stimuli provided to the subject on display 110.

VR/AR headgear 108 also includes an eye tracking unit 116 for tracking eye movements of the subject is response to the plurality of visual stimuli provided to the subject on display 110. Eye tracking unit 116 may include a plurality of infrared cameras for tracking eye movements of the user.

System 100 further includes a machine learning model 118 which deciphers normal patterns and abnormal patterns obtained based on measurement data from gyroscope 112, inertial measurement unit 114, and eye tracking unit 116.

Based on the output of machine learning model 118, a comprehensive report is generated pertaining to assessment of posture and stability of the subject, using machine learning model 118.

In accordance with an embodiment, system 100 includes a base plate 120 upon which the subject stands. Movements such as, but not limited to, forward movements, backward movements, and vibrations are provided by base plate 120 for providing stimuli to the subject standing on base plate 120. The vibrations of base plate 120 remove the proprioceptive input from the legs of the subject.

Figure 4:
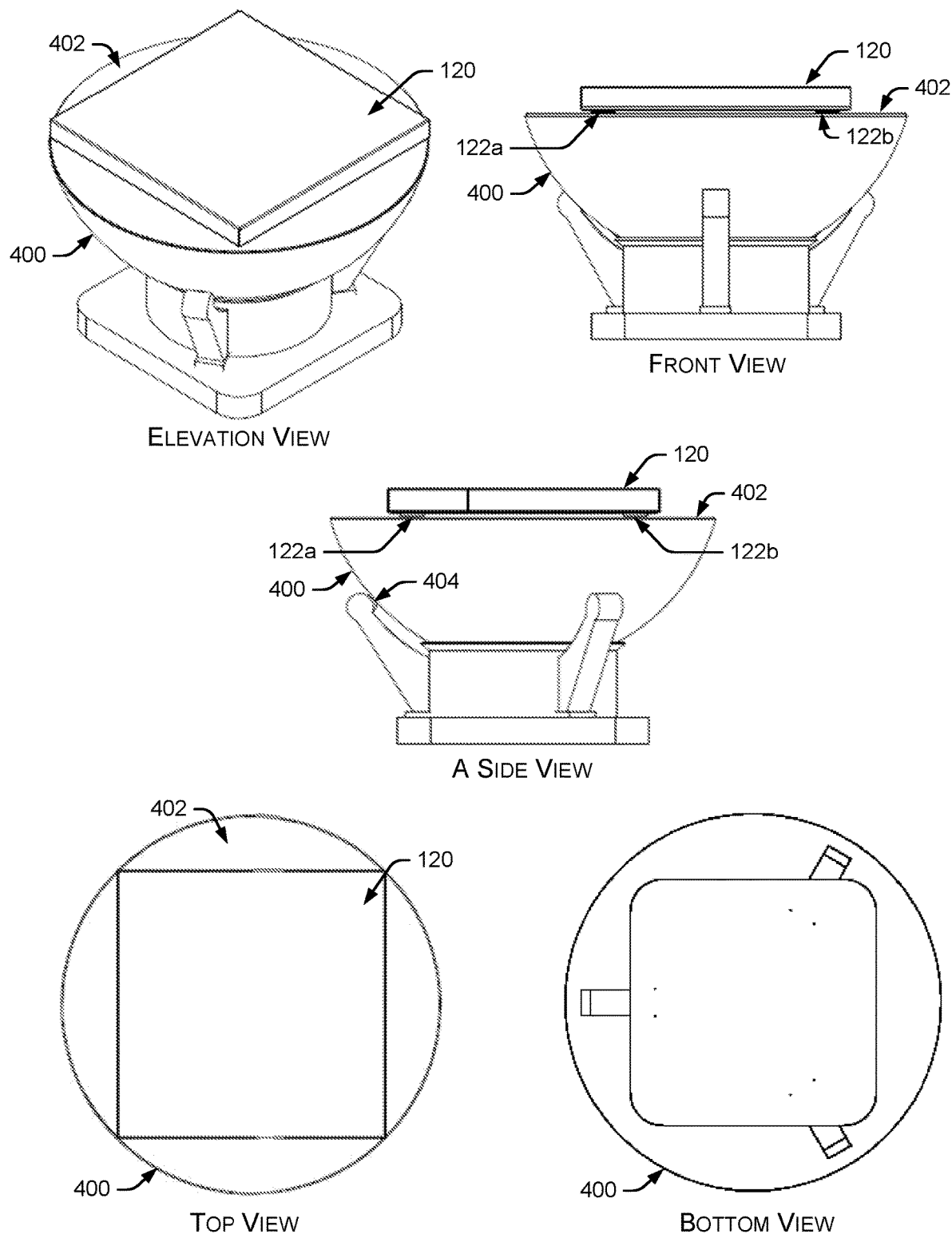
FIG. 4 is a diagram of an example system for assessing a balance and posture of a subject.
Figure 5:
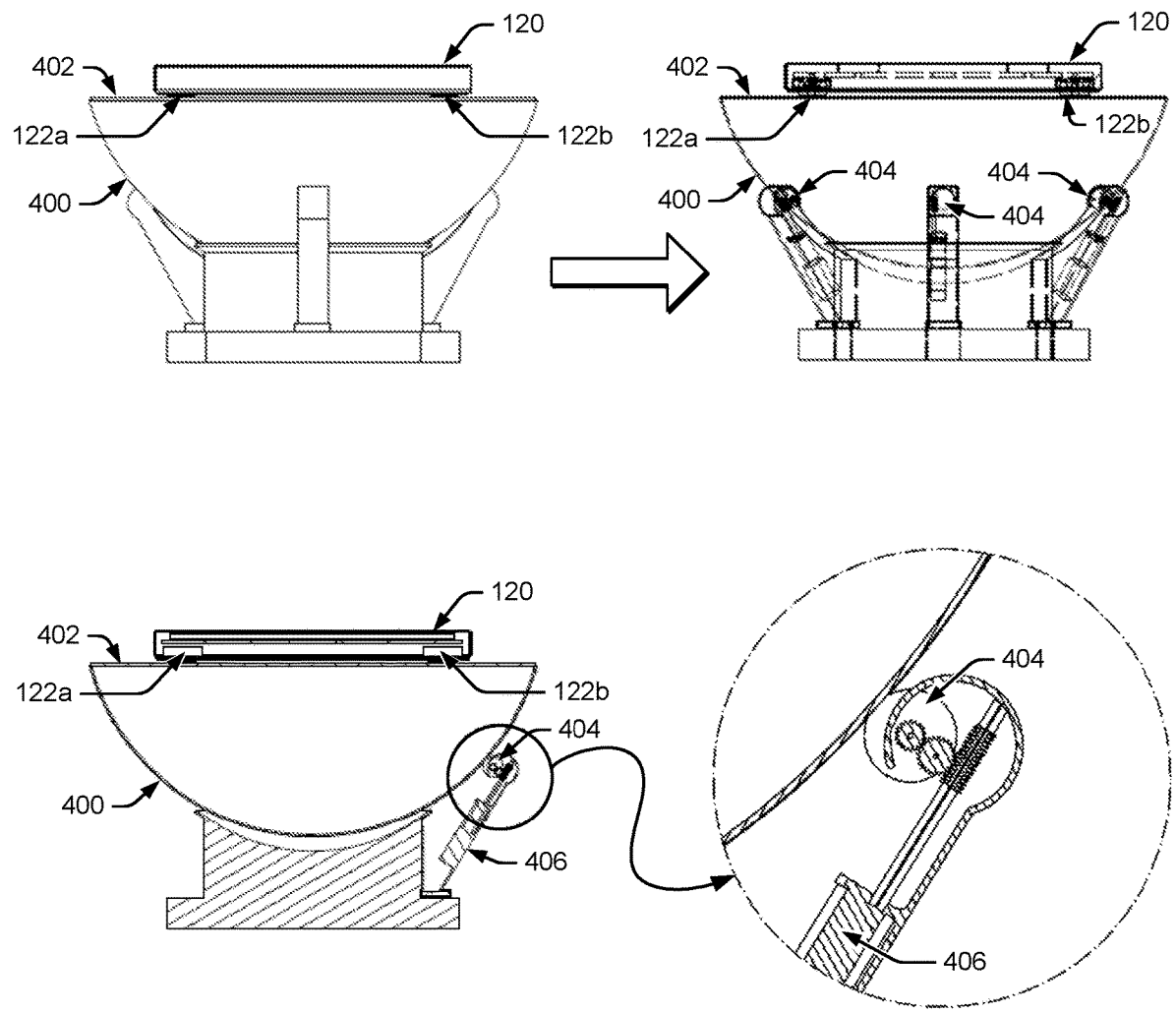
FIG. 5 is a diagram of the example system for assessing a balance and posture of a subject of FIG. 4, showing an example base plate, hemispherical top, spherical rollers, motors, and a plurality of strain gauge sensors.

In accordance with another embodiment, base plate 120 is further subjected oscillatory movements and yaw rotations, while the subject stands on base plate 120. For example, balance systems need to be tested using controlled tests which represent real life scenarios. In accordance with the embodiment shown in FIGS. 4-5, base plate 120 is implemented on as a hemispherical platform 400 which has a hemispherical shape with the flat surface 402 up and with three spherical rollers 404 connected to the bottom of the hemispherical platform 400. The three spherical rollers 404 are connected to three motors 406 and are controlled by software to cause the desired configuration of motion of the flat surface 402 of the hemispherical platform 400. Further, four of the strain gauges 122a, 122b, . . . 122n are mounted on top of the flat surface 402 of the hemispherical platform 400 to sense and calculate the change in center of balance of the subject. Using this hemispherical platform 400, motions such as, for example, movements like a rocking boat may be simulated, and subjects are tested for balance under such conditions.

A plurality of strain gauge sensors 122a-122n are fitted to corners of base plate 120. Each strain gauge sensor of plurality of strain gauge sensors 122a-122n measures a center of gravity of the subject in response to movements of base plate 120.

Processor 102 is further configured to detect a shift in the center of gravity of the subject based on differences in measurement of center of gravity obtained from plurality of strain gauge sensors 122a-122n.

Thereafter, machine learning model 118 is utilized to decipher normal patterns and abnormal patterns based on measurement data from gyroscope 112, measurement data from inertial measurement unit 114, measurement data from eye tracking unit 116, and data pertaining to shift in the center of gravity of the subject.

A comprehensive report is then generated pertaining to an assessment of posture and stability of the subject based on utilizing machine learning model 118.

In accordance with another embodiment, VR/AR headgear 108 worn by the subject is a pair of augmented reality googles. The augmented reality goggles are used for testing the postural stability and gait of the subject in a dynamic environment while the subject is carrying out a normal walk.

Figure 2:
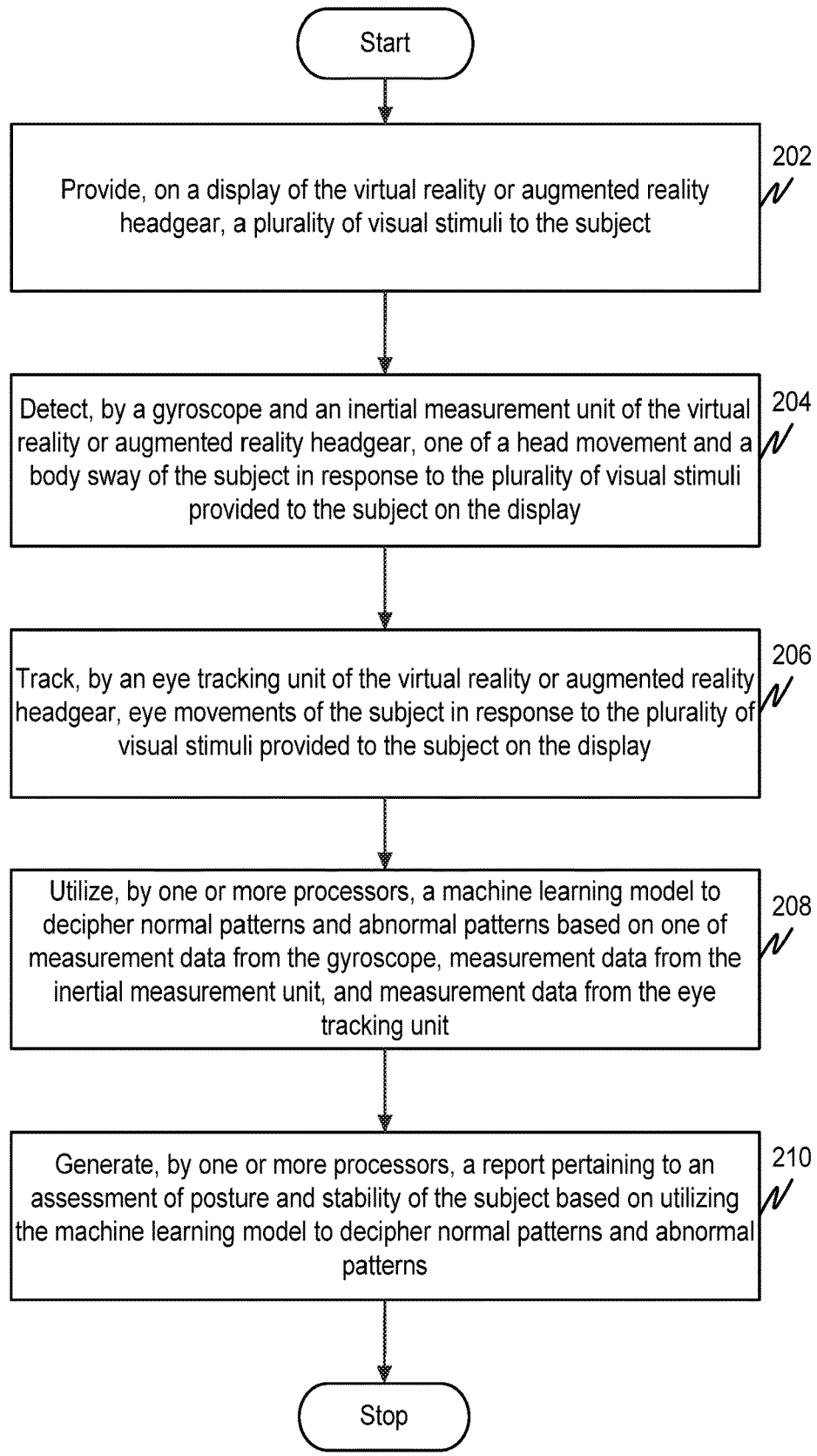
FIG. 2 illustrates a flowchart of a method for assessing a balance and posture of a subject in accordance with an embodiment of the invention.

FIG. 2 illustrates a flowchart of a method for assessing a balance and posture of a subject using VR/AR headgear 108 worn by the subject in accordance with an embodiment of the invention.

As illustrated in FIG. 2, in step 202, a plurality of visual stimuli are provided to the subject via display 110. In step 204, head movements and body sway of the subject in response to the plurality of visual stimuli are detected using gyroscope 112 and inertial measurement unit 114.

In step 206, eye movements of the subject in response to the plurality of visual stimuli provided to the subject on display 110, are tracked using eye tracking unit 116.

In an ensuing step 208, machine learning model 118 is utilized to decipher normal patterns and abnormal patterns based on measurement data from gyroscope 112, measurement data from inertial measurement unit 114, and measurement data from eye tracking unit 116.

At step 210, a comprehensive report is generated pertaining to an assessment of posture and stability of the subject, utilizing machine learning model 118.

Figure 3:
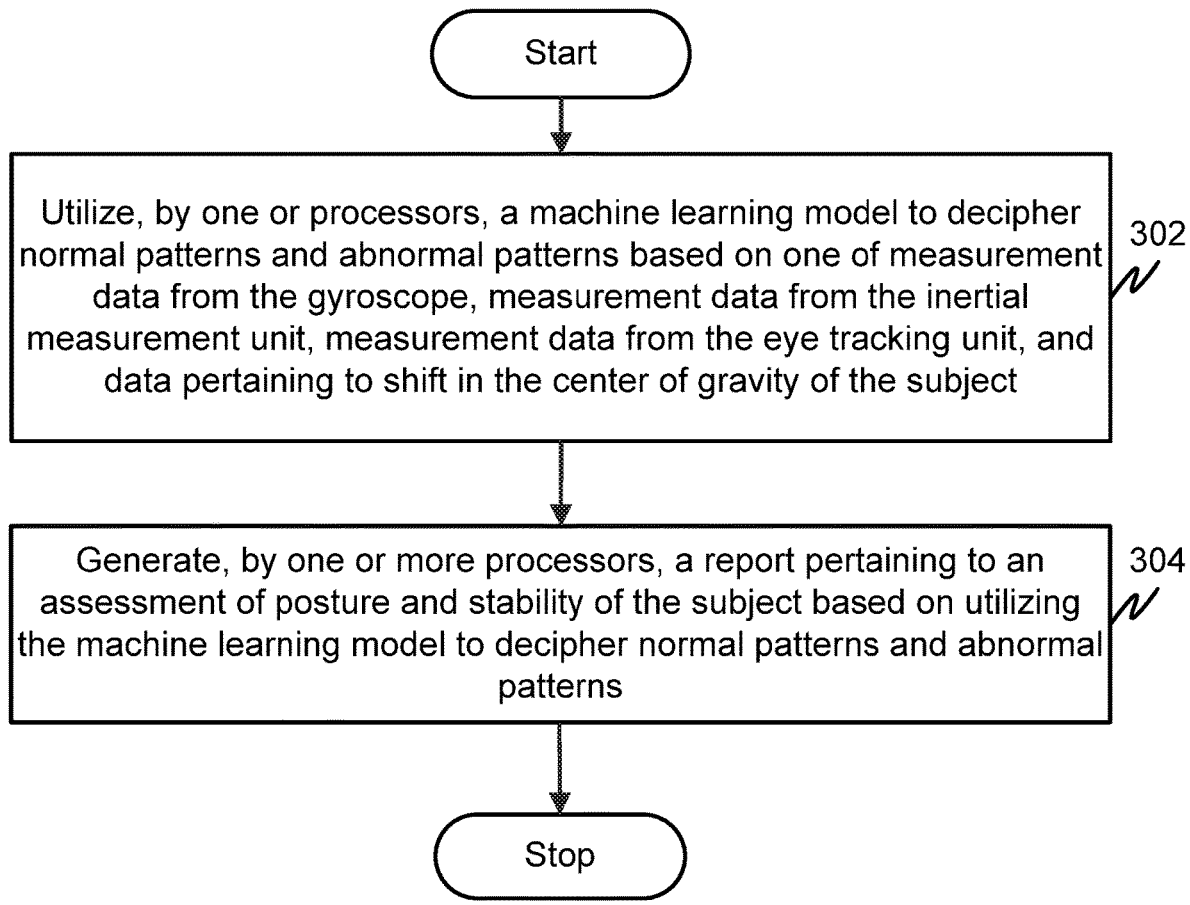
FIG. 3 illustrates a flowchart of a method for assessing posture and balance of the subject using a VR/AR headgear and a base plate fitted with a plurality of strain gauge sensors in accordance with an exemplary embodiment of the invention.

FIG. 3 illustrates a flow chart of a method for assessing posture and balance of the subject using VR/AR headgear 108 and base plate 120 fitted with plurality of strain gauge sensors 122a-122n in accordance with an exemplary embodiment of the invention.

In step 302, machine learning model 118 is utilized to decipher normal patterns and abnormal patterns based on measurement data from gyroscope 112, measurement data from inertial measurement unit 114, measurement data from eye tracking unit 116, and data pertaining to shift in the center of gravity of the subject obtained from plurality of strain gauge sensors 122a-122n.

At step 304, a comprehensive report is generated pertaining to an assessment of posture and stability of the subject, utilizing machine learning model 118.

In another embodiment, VR/AR headgear 108 is a pair of augmented reality goggles to test postural stability and gait of the subject in a dynamic environment while the subject is carrying out a normal walk.

The invention uses a specially designed VR/AR headgear for providing immersive environment to the patient. The VR/AR headgear includes a gyroscope and an inertial measurement unit (IMU) or acceleroscope to detect head movement and body sway of the subject in the testing environment.

Instead of force plates, the invention utilizes specially designed strain gauges to detect shift in center of gravity. There are four stain gauge sensors which are placed at the four corners of the base plate and the processor detects the difference in the four strain gauge sensors to determine the shift in center of gravity.

Further, the VR/AR headgear tracks eye movements during the test. The base plate, in addition to forward and backward movement, also has vibrations to remove the proprioceptive input from the legs. The base plate is further subjected oscillatory movements and yaw rotations, while the subject stands on the base plate.

The invention utilizes machine learning models and algorithms to combine inputs from the strain gauges, the IMU, and the eye tracking unit to give a comprehensive report about the subject's balance system.

The invention is also used to test the subject in an environment more pertinent in the real world, when the subject is walking normally. The invention uses wireless augmented reality goggles with eye tracking and IMU to test postural stability and gait in a dynamic environment while the subject is carrying out a normal walk.

Those skilled in the art will realize that the above recognized advantages and other advantages described herein are merely exemplary and are not meant to be a complete rendering of all of the advantages of the various embodiments of the invention.

The system, as described in the invention or any of its components may be embodied in the form of a computing device. The computing device can be, for example, but not limited to, a general-purpose computer, a programmed microprocessor, a micro-controller, a peripheral integrated circuit element, and other devices or arrangements of devices, which can implement the steps that constitute the method of the invention. The computing device includes a processor, a memory, a nonvolatile data storage, a display, and a user interface.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A system for assessing a balance and posture of a subject, the system comprising:
   a memory;
   a processor communicatively coupled to the memory; and
   a virtual reality or augmented reality headgear worn by the subject, the virtual reality or augmented reality headgear communicatively coupled to the memory and the processor and providing an immersive environment to the subject, the virtual reality or augmented reality headgear comprising:
   a display for providing a plurality of visual stimuli to the subject;
   a gyroscope and an inertial measurement unit to detect one of a head movement and a body sway of the subject in response to the plurality of visual stimuli provided to the subject on the display; and
   an eye tracking unit for tracking eye movements of the subject in response to the plurality of visual stimuli provided to the subject on the display;
   wherein the processor is configured to:
   utilize a machine learning model to decipher normal patterns and abnormal patterns based on one of measurement data from the gyroscope, measurement data from the inertial measurement unit, and measurement data from the eye tracking unit; and
   generate a report pertaining to an assessment of posture and stability of the subject based on utilizing the machine learning model to decipher normal patterns and abnormal patterns of the balance and posture of the subject;
   a base plate upon which the subject stands, and a plurality of strain gauge sensors fitted to corners of the base plate, wherein each strain gauge sensor of the plurality of strain gauge sensors measures a center of gravity of the subject in response to movements of the base plate;
   wherein the base plate is implemented on a hemispherical platform, with a top flat surface and a hemispherical bottom, wherein four strain gauges are mounted on top of the flat surface of the hemispherical platform;

wherein the system further comprises three spherical rollers connected to the bottom of the hemispherical platform, the three spherical rollers connected to three respective motors; and the three respective motors are controlled by software to cause a desired configuration of motion of the top flat surface of the hemispherical platform.

2. The system as claimed in claim 1, wherein the movements of the base plate comprise forward movements, backward movements, incline motions and vibrations, wherein the vibrations remove proprioceptive input from legs of the subject.

3. The system as claimed in claim 1, wherein the base plate is further subjected to oscillatory movements and yaw rotations, while the subject stands on the base plate.

4. The system as claimed in claim 1, wherein the processor is configured to detect a shift in the center of gravity of the subject based on differences in measurement of center of gravity obtained from the plurality of strain gauge sensors.

5. The system as claimed in claim 4, wherein the processor is configured to:
utilize a machine learning model to decipher normal patterns and abnormal patterns based on one of measurement data from the gyroscope, measurement data from the inertial measurement unit, measurement data from the eye tracking unit, and measurement data of the shift in the center of gravity of the subject obtained from the plurality of strain gauge sensors; and
generate a report comprising an assessment of posture and stability of the subject based on the machine learning model to decipher normal patterns and abnormal patterns of the balance and posture of the subject.

6. The system as claimed in claim 1, wherein the virtual reality or augmented reality headgear worn by the subject comprises a pair of augmented reality goggles to test postural stability and gait of the subject in a dynamic environment while the subject is walking.

7. The system of claim 1, wherein the machine learning model is trained with controlled tests representing real life scenarios to decipher the normal patterns and the abnormal patterns of the balance and posture of the subject.

8. A method for assessing a balance and posture of a subject using a virtual reality or augmented reality headgear worn by the subject, the method comprising:
providing, on a display of the virtual reality or augmented reality headgear, a plurality of visual stimuli to the subject;
detecting, by a gyroscope and an inertial measurement unit of the virtual reality or augmented reality headgear, one of a head movement and a body sway of the subject in response to the plurality of visual stimuli provided to the subject on the display;
tracking, by an eye tracking unit of the virtual reality or augmented reality headgear, eye movements of the subject in response to the plurality of visual stimuli provided to the subject on the display;
utilizing, by one or more processors, a machine learning model to decipher normal patterns and abnormal patterns of the balance and posture of the subject based on one of measurement data from the gyroscope, measurement data from the inertial measurement unit, and measurement data from the eye tracking unit;
generating, by one or more processors, a report comprising an assessment of the posture and a stability of the subject based on utilizing the machine learning model to decipher the normal patterns and the abnormal patterns of the balance and posture of the subject;
measuring, by each strain gauge sensor of a plurality of strain gauge sensors, a center of gravity of the subject in response to movements of a base plate upon which the subject stands, wherein the plurality of strain gauge sensors are fitted to corners of the base plate;
measuring the center of gravity of the subject in response to movements of the base plate, wherein the base plate is implemented on a hemispherical platform, with a top flat surface and a hemispherical bottom;
measuring the center of gravity of the subject in response to movements of the base plate, wherein the base plate further comprises three spherical rollers connected to the hemispherical bottom of the hemispherical platform, the three spherical rollers connected to three respective motors; and
controlling the three respective motors by software to cause a desired configuration of motion of the top flat surface of the hemispherical platform.

9. The method as claimed in claim 8, wherein the movements of the base plate comprise forward movements, backward movements, incline motions and vibrations, wherein the vibrations remove proprioceptive input from the legs of the subject.

10. The method as claimed in claim 8, wherein the base plate is further subjected to oscillatory movements and yaw rotations, while the subject stands on the base plate.

11. The method as claimed in claim 8, wherein the measuring comprises detecting, by one or more processors, a shift in the center of gravity of the subject based on differences in measurement of center of gravity obtained from the plurality of strain gauge sensors.

12. The method as claimed in claim 11 further comprising:
utilizing, by one or processors, a machine learning model to decipher the normal patterns and the abnormal patterns based on one of measurement data from the gyroscope, measurement data from the inertial measurement unit, measurement data from the eye tracking unit, and measurement data of the shift in the center of gravity of the subject obtained from the plurality of strain gauge sensors; and
generating, by one or more processors, a report comprising an assessment of the posture and the stability of the subject based on utilizing the machine learning model to decipher the normal patterns and the abnormal patterns of the balance and posture of the subject.

13. The method as claimed in claim 8, wherein the virtual reality or augmented reality headgear worn by the subject comprises a pair of augmented reality goggles to test a postural stability and a gait of the subject in a dynamic environment while the subject is walking.

14. The method of claim 8, further comprising training the machine learning model with controlled tests representing real life scenarios to decipher the normal patterns and the abnormal patterns of the balance and posture of the subject.

* * * * *